(12) United States Patent
Nadano et al.

(10) Patent No.: US 6,177,595 B1
(45) Date of Patent: Jan. 23, 2001

(54) PROCESS OF PRODUCING CHLOROFLUOROACETONES

(75) Inventors: Ryo Nadano; Takashi Sakaya; Mineo Watanabe; Yoshihiko Goto, all of Saitama; Toshihiro Nakamichi; Shigeru Suenaga, both of Yamaguchi, all of (JP)

(73) Assignee: Central Glass Company, Limited, Ube (JP)

( * ) Notice: Under 35 U.S.C. 154(b), the term of this patent shall be extended for 0 days.

(21) Appl. No.: 09/393,698

(22) Filed: Sep. 10, 1999

(30) Foreign Application Priority Data

Sep. 11, 1998 (JP) .................................................. 10-258192
Jul. 9, 1999 (JP) .................................................. 11-195714

(51) Int. Cl.[7] .................................................. C07C 45/63
(52) U.S. Cl. .......................... 568/394; 568/411; 568/419; 570/168
(58) Field of Search .................................. 568/394, 393, 568/419, 411; 570/166, 206, 168

(56) References Cited

U.S. PATENT DOCUMENTS 5,905,174  5/1999  Kanai et al. .......................... 568/411
6,023,004 * 2/2000  Thenappan et al. ................. 570/188

FOREIGN PATENT DOCUMENTS 10-287609  10/1998  (JP) .
11-1451    1/1999   (JP) .

OTHER PUBLICATIONS

English translation of Zeifman et al., "Polyfluorinated Al–Enolates". Doklady Akademii Nauk SSSR, vol. 307, No. 6, pp. 1385–1390, Aug. 1989.

* cited by examiner

*Primary Examiner*—Sreeni Padmanabhan
(74) *Attorney, Agent, or Firm*—Evenson, McKeown, Edwards & Lenahan, P.L.L.C.

(57) ABSTRACT

A process of producing chlorofluoroacetones represented by a general formula

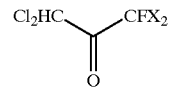

where X represents independently chlorine atom or fluorine atom. The production process comprises fluorinating in a liquid phase pentachloroacetone by hydrogen fluoride in the presence of a catalyst comprising tin tetrahalide.

12 Claims, No Drawings

PROCESS OF PRODUCING CHLOROFLUOROACETONES

BACKGROUND OF THE INVENTION

1. Field of the Invention

This invention relates to improvements in a process of producing chlorofluoroacetones, particularly 3,3-dichloro-1,1,1-trifluoroacetone and 1,1,3,3-tetrachloro-1-fluoroacetone, which are useful as intermediate materials of medicines and agricultural chemicals and as reagents for introducing fluorine-containing groups.

2. Description of the Prior Art

A variety of processes of producing chlorofluoroacetones have been hitherto proposed and put into practical use. For example, an English translation (pages 241 to 245) of Doklady Akademii Nauk SSSR, Vol. 307, No. 6, pages 1385 to 1390, August 1989 discloses that 3,3-dichloro-1,1,1-trifluoroacetone is synthesized from 3,3,3-trichloro-1,1,1-trifluoropropane-2-one in an anhydrous solvent, through an Al-enolate intermediate, by using a mercury compound as a catalyst. Additionally, Japanese Patent Provisional Publication No. 10-287609 discloses that pentachloroacetone is fluorinated by hydrogen fluoride in a liquid phase in the presence of an antimony pentachloride thereby to form 3,3-dichloro-1,1,1-trifluoroacetone. Further, Japanese Patent Provisional Publication No. 11-1451 discloses that pentachloroacetone is fluorinated in a gas phase in the presence of a fluorination catalyst thereby to form 3,3-dichloro-1,1,1-trifluoroacetone.

The technique disclosed in the English translation of Doklady Akademii Nauk SSSR not only requires to maintain a production process strictly in an anhydrous condition but also uses mercury, which is problematic in case of employing the technique in an industrial scale. The technique disclosed in Japanese Patent Provisional Publication No. 10-287609 uses the antimony pentachloride catalyst and therefore provides corrosion of a reactor, which is problematic as an industrial process. Further, by the technique disclosed in Japanese Patent Provisional Publication No. 11-1451, a relatively large amount of reduction products such as 3-chloro-1,1,1-trifluoroacetone and 1,1,1-trifluoroacetone is produced.

SUMMARY OF THE INVENTION

It is an object of the present invention to provide an improved process of producing chlorofluoroacetones, which can overcome drawbacks encountered in the above conventional techniques.

Another object of the present invention is to provide an improved process of producing chlorofluoroacetones, which is suitable for being carried out in an industrial scale.

A further object of the present invention is to provide an improved process of producing chlorofluoroacetones, which is high in yield of chlorofluoroacetones while suppressing corrosion of a reactor in such an extent as to be allowable.

A process according to the present invention is for producing chlorofluoroacetones represented by a general formula

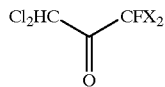

where X represents independently chlorine atom or fluorine atom. The process comprises fluorinating in a liquid phase pentachloroacetone by hydrogen fluoride in the presence of a catalyst containing at least one metal selected from the group consisting of metals of the groups 4, 5, 6, 7, 8, 14 and 15 of the periodic table, the metals excluding antimony.

According to the production process of the present invention, objective chlorotrifluoroacetone, particularly 3,3-dichloro-1,1,1-trifluoroacetone and 1,1,3,3-tetrachloro-1-fluoroacetone, can be effectively produced from the corresponding organic chlorinated compound under a single step reaction.

DETAILED DESCRIPTION OF THE INVENTION

According to the present invention, a process of producing chlorofluoroacetones represented by the following general formula (1):

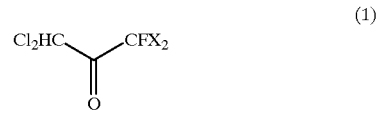

(1)

where X represents independently chlorine atom or fluorine atom. The process comprises fluorinating in a liquid phase pentachloroacetone by hydrogen fluoride in the presence of a catalyst containing at least one metal selected from the group consisting of metals of the groups 4, 5, 6, 7, 8, 14 and 15 of the periodic table, the metals excluding antimony.

According to the production process of the present invention, chlorine atoms in —$CCl_3$ group of pentachloroacetone are successively substituted with fluorine atom, and therefore intermediately produced lower fluorine compounds may be used in place of pentachloroacetone, which is also a mode of the present invention.

Chlorofluoroacetones represented by the general formula (1) are 3,3-dichloro-1,1,1-trifluoroacetone, 1,3,3-trichloro-1,1-difluoroacetone and 1,1,3,3-tetrachloro-1-fluoroacetone, and preferably 3,3-dichloro-1,1,1-trifluoroacetone and/or 1,1,3,3-tetrachloro-1-fluoroacetone.

The production process according the present invention can be carried out as a batch process, a half-batch process in which reaction is conducted removing only products from a reactor, and a continuous or flowing process. While discussion will be made mainly on reaction in the batch process hereinafter, it will be appreciated that reaction conditions (discussed below) for the reaction in the batch process may be applicable to other processes upon being modified to such extents as to be readily adjustable by persons skilled in the art.

Pentachloroacetone used as a starting (raw) material in the production process of the present invention can be synthesized by known methods, for example, usually by chlorinating acetone with chlorine in the presence of light or a catalyst such as metal chloride, acid, metal-organic acid salt, or by oxidizing chlorinated alcohol.

The catalyst to be used in the production process of the present invention includes at least one metal compound containing one of metals of the groups 4, 5, 6, 7, 8, 14 and 15 of the periodic table, the metals excluding antimony. Antimony is high in fluorination activity so that reaction can proceed within a short time; however, it is high in corrosion action to a metal reactor and therefore is not preferable to be used as catalyst. It is preferable to use for the catalyst tin, titanium, molybdenum, tantalum, lead, manganese, niobium, bismuth, tungsten and/or iron, in which tin is more preferable. Specifically, it is preferable to use as the catalyst only tin compound, or a combination (mixture) of tin compound and at least one of compounds of titanium, molybdenum, tantalum, lead, manganese, niobium, bismuth, tungsten and iron, in which the combination of tin compound and titanium compound, or the combination of tin compound and niobium compound is more preferable.

According to kinds of the catalyst, modes of reaction in the production process change. In case of using the catalyst of only tin compound, reaction proceeds relatively gently so that a relatively long reaction time is required, providing advantage of producing less by-products. In case of using the catalyst of the combination of tin compound and titanium compound or the combination of tin compound and niobium compound, formation of decarbonylation product is found while providing advantage of completing reaction within a relatively short time. Additionally, it is more preferable to use only tin compound mainly in case of producing 1,1,3,3-tetrachloro-1-fluoroacetone. In any cases of the above-mentioned, requirements for industrial production processes can be sufficiently met.

It is assumed that the metal compound serving as the catalyst takes the form of a specified compound according to conditions of a reaction system of the fluorination, and therefore it is unnecessary that the metal compound in the form of a specified compound when supplied into a reactor. Accordingly, the metal compound to be supplied to the reactor is in the form of chloride, bromide, fluoride, oxide, nitrate, sulfate, carbonate and/or the like of the above-mentioned metal, in which chloride or fluoride is preferable. It is preferable that the metal of the metal compound is one in the state of higher valence which are usually takable, such as tin having the valence of 4, titanium having the valence of 4, molybdenum having the valence of 5, tantalum having the valence of 5, lead having the valence of 4, manganese having the valence of 4, niobium having the valence of 5, bismuth having the valence of 4, tungsten having the valence of 6 and/or iron having the valence of 3.

More specifically, the compound of tin is preferably halide such as tin tetrachloride, tin dichloride, tin tetrafluoride, tin difluoride, tin tetrabromide, tin dibromide, tin tetraiodide, and tin diiodide, in which tin tetrachloride is more preferable. The compound of titanium is preferably titanium tetrachloride, titanium trichloride, and/or titanium tetrabromide. The compound of molybdenum is preferably molybdenum pentachloride. The compound of tantalum is preferably tantalum pentachloride and/or tantalum pentafluoride. The compound of lead is preferably lead tetrachloride. The compound of manganese is preferably manganese tetrachloride. The compound of niobium is preferably niobium pentachloride. The compound of bismuth is preferably bismuth tetrachloride and/or bismuth trichloride. The compound of tungsten is preferably tungsten hexafluoride. The compound of iron is preferably ferric chloride.

In the production process of the present invention, the amount of tin compound in the catalyst to be required is within a range of 0.001 to 0.5 mol, preferably 0.01 to 0.3 mol, more preferably 0.05 to 0.2 mol relative to 1 mol of pentachloroacetone. If the amount is less than 0.001 mol, a reaction rate of petachloroacetone and a yield of chlorofluoroacetones represented by the general formula (1) are lowered. If the amount exceeds 0.5 mol, the production amount of tarry material formed of high boiling point compounds are increased.

In production of 3,3-dichloro-1,1,1-trifluoroacetone, the amount of at least one metal compound other than the tin compound in the catalyst to be required is about within a range of 0.1 to 1 mol, preferably 0.2 to 0.5 mol relative to 1 mol of the tin compound. If the amount is less than 0.2 mol, the reaction rate of pentachloroacetone and the yield of 3,3-dichloro-1,1,1-trifluoroacetone are lowered. If the amount exceeds 1 mol, the production amount of tarry material is increased, and/or the production amount of excessively fluorinated product is increased. However, in the production of 1,1,3,3-tetrachloro-1-fluoroacetone, it is sufficient to use only tin compound as the catalyst, so that it is usually unnecessary to add the metal compound(s) other than tin compound as the catalyst, as discussed above.

A reaction temperature in the production process is within a range of from 50 to 250° C., preferably 80 to 230° C., more preferably 100 to 200° C., further more preferably 130 to 170° C. If the reaction temperature is lower than 50° C., the reaction rate of pentachloroacetone and the yield of chlorofluoroacetones represented by the general formula (1) are lowered. If the reaction temperature exceeds 250° C., the production amount of tarry material is increased, and/or the production amount of excessively fluorinated product is increased.

In the reaction system, a molar ratio of hydrogen fluoride relative to pentachloroacetone serving as the starting material is within a range of from 3 to 50, preferably 5 to 30, more preferably 8 to 20, though the range is different according to the number of fluorine atoms in the objective product. If the molar ratio is less than 3, the reaction rate of pentachloroacetone is not sufficiently high. Even if the molar ratio exceeds 50, further improvement in reaction rate of pentachlorocetone cannot be recognized while proving economical disadvantage from the viewpoint of recovery of unreacted hydrogen fluoride.

A reaction pressure depends on the reaction temperature. It is sufficient that a reaction mixture in the reactor can be kept in the state of liquid phase under the reaction pressure. Therefore, the reaction pressure is within a range of preferably 1.0 to 100 kg/cm$^2$, more preferably 5 to 70 kg/cm$^2$.

In the reaction system, solvent may be present for the purpose of adjusting reaction and preventing catalyst deterioration. In this case, it is preferable to use as the solvent 1,3-bis(trifluoromethyl)benzene, or 2,4-dichloro-1-(trifluoromethyl)benzene, or the like which cannot be readily fluorinated nor chlorinated.

The reactor in which the reaction of the fluorination is conducted is preferably made of a corrosion-resistant metal such as Hastelloy™, stainless steel, Monel metal, nickel or the like, or configured such that the inside surface of the reactor is lined with the above corrosion-resistant metal, polytetrafluoroethylene resin, polychlorofluoroethylene resin, polyvinylidene fluoride resin, or PFA resin (perfluoroalkylvinylether).

Hereinafter, the production process of the present invention will be discussed in detail on a case using the batch process.

Hydrogen fluoride, and tin tetrachloride and the like (as the catalysts) are supplied into the reactor which is endurable to a pressure required under the reaction conditions. The order of supplying hydrogen fluoride, and tin tetrachloride and the like into the reactor is not particularly limited. Pentachloroacetone has been previously supplied into the reactor before supply of hydrogen fluoride and the catalyst (s), or may be supplied after supply of hydrogen fluoride and the catalyst(s). The reactor is set as a closed system and gradually heated from the outside thereof upon continuous stirring, in which the inside pressure of the reactor rises with proceeding of reaction in the reactor. In case that pentachloroacetone has not been previously supplied in the reactor, pentachloroacetone may be introduced under pressure into the reactor when the inside temperature of the reactor reaches a suitable temperature such as about 40° C.

Then, the reactor is further heated so that the inside pressure of the reactor rises. In case that the reactor is sufficiently high in pressure-withstanding ability, the pressure is allowed to further rise. However, hydrogen chloride produced under reaction may be flowed through a reflux condenser disposed at the upper part of the reactor so as to suppress the pressure under reaction at a certain value. Heating is stopped when it is confirmed that the objective product is formed in the reactor by analyzing the content of the reactor by a gas chromatograph or by measuring the amount of hydrogen chloride flowed of the reactor. Then, the reactor is cooled, and subsequently gas (mainly including hydrogen chloride and hydrogen fluoride) within the reactor is purged. Organic compounds (including synthesized chlorofluorocetone) and remaining hydrogen fluoride can be recovered through the reflux condenser, or may be taken out in the state of liquid from the reactor.

Chlorofluoroacetones produced in the above manner according to the present invention and represented by the general formula (1) can be purified by applying known purifying methods which have been established for similar reaction products obtained under fluorination. For example, after chlorofluoroacetones are taken out in the state of liquid or gas together with hydrogen chloride, unreacted hydrogen fluoride, hydrogen chloride and excessive hydrogen fluoride are removed by distillation or liquid phase separation. Subsequently, acid component remaining in chlorofluoroacetones is removed by using basic material, and then chlorofluoroacetones are subjected to rectification thereby obtaining a high purity chlorofluoroactone represented by the general formula (1).

The following examples are included merely to aid in the understanding of the invention, and variations may be made on the examples by one skilled in the art without departing from the spirit and scope of the invention.

EXAMPLE 1

A 500-ml autoclave made of stainless steel (SUS 316L) equipped with a reflux condenser and a stirrer was charged with 35 g of tin tetrachloride and 11 g of hydrogen fluoride. Then, stirring of a content in the autoclave was started at room temperature (about 15° C.), and the autoclave was gradually heated to raise the temperature inside the autoclave so that the inside pressure of the autoclave rose. Upon lapse of about 6 hours after the starting of heating autoclave, the inside temperature and pressure of the autoclave reached respectively 130° C. and about 22 kg/cm² (gage pressure). At this time, heating of the autoclave was stopped, upon which the autoclave was further charged with 201 g of pentachloroacetone and 199 g of hydrogen fluoride. Then, the autoclave was again heated to gradually raise the inside temperature of the autoclave thereby allowing reaction to be initiated. Upon lapse of 37 hours after charging of pentachloroacetone, the inside temperature and pressure of the autoclave reached respectively 160° C. and about 45 kg/cm² (gage pressure). At this time, heating of the autoclave was stopped so as to cool the content of the autoclave. After cooling, the temperature of the reflux condenser was adjusted at 20° C., upon which the inside temperature of the autoclave was raised again to 50° C. so that hydrogen fluoride was distilled out. Thereafter, the inside temperature of the reactor was raised to 120° C. thereby conducting flash distillation without allowing the effluent to pass through the reflux condenser, thus obtaining 140 g of organic compounds. The thus obtained organic compounds were subjected to analysis using a gas chromatograph. As a result, it was confirmed that the organic compounds contained 78.7 area % of 3,3-dichloro-1,1,1-trifluoroacetone, 7.7 area % of 1-chloro-1,3,3,3-tetrafluoroacetone, 2.1 area % of 1,3,3-trichloro-1,1-difluoroacetone, 1.9 area % of 1,1,3,3-tetrachloro-1-fluoroacetone, and other substances.

EXAMPLE 2

A 500-ml autoclave made of stainless steel (SUS 316L) equipped with a reflux condenser and a stirrer was charged with 201 g of pentachloroacetone, 35 g of tin tetrachloride and 210 g of hydrogen fluoride. Then, stirring of a content in the autoclave was started at room temperature (about 15° C.), and the autoclave was gradually heated to raise the temperature inside the autoclave so that the inside pressure of the autoclave rose. Upon lapse of about 18 hours after the initiation of reaction, the inside temperature and pressure of the autoclave reached respectively 147° C. and 35 kg/cm² (gage pressure). At this time, heating of the autoclave was stopped so that the content of the autoclave was cooled. After cooling, the temperature of the reflux condenser was adjusted at 20° C., upon which the inside temperature of the autoclave was raised again to 50° C. so that hydrogen fluoride was distilled out. Thereafter, the inside temperature of the reactor was raised to 120° C. thereby conducting flash distillation under reduced pressure without allowing the effluent to pass through the reflux condenser, thus obtaining 175 g of organic compounds. The thus obtained organic compounds were subjected to analysis using a gas chromatograph. As a result, it was confirmed that the organic compounds contained 5.8 area % of 3,3-dichloro-1,1,1-trifluoroacetone, 0.3 area % of 1,3-dichloro-1,1,3-trifluoroacetone, 5.8 area % of 1,3,3-trichloro-1,1-difluoroacetone, 81.5 area % of 1,1,3,3-tetrachloro-1-fluoroacetone, and other substances.

EXAMPLE 3

A 2-liter autoclave made of stainless steel (SUS 316L) equipped with a reflux condenser and a stirrer was charged with 78 g of tin tetrachloride, 11 g of titanium tetrachloride and 440 g of hydrogen fluoride. Then, heating of the autoclave was started upon which the temperature of a content (liquid) of the autoclave was reached to 40° C. Stirring of the content of the autoclave was continued for 1 hour from a time at which the temperature of the content had reached 40° C. Then, the autoclave was further charged with 485 g of pentachloroacetone as a raw material. Then, the autoclave was again heated to gradually raise the inside temperature of the autoclave thereby allowing the reaction to be initiated. Upon lapse of 2 hours after initiation of the reaction, the inside temperature and pressure of the autoclave reached respectively 140° C. and 35 kg/cm² (gage pressure), in which the reaction was continued maintaining the pressure at 35 kg/cm² (gage pressure) while hydrogen chloride was emitted through the reflux condenser. Upon lapse of 18 hours after initiation of the reaction, the moles of hydrogen chloride purged reached 3 times of the moles of the raw material. At this time, heating of the autoclave was stopped to cool the content of the autoclave. After cooling, the temperature of the reflux condenser was adjusted at 20° C., upon which the inside temperature of the autoclave was raised again to 50° C. so that hydrogen fluoride is distilled out. Thereafter, the inside temperature of the reactor was raised to 120° C. thereby conducting flash distillation without allowing the effluent to pass through the reflux condenser, thus obtaining 248 g of organic compounds. The thus obtained organic compounds were subjected to analysis using a gas chromatograph. As a result, it was confirmed that the organic compounds contained 63.7 area % of 3,3-dichloro-1,1,1-trifluoroacetone, 14.9 area % of 1-chloro-1,3,3,3-tetrafluoroacetone, 3.7 area % of 1,3,3-trichloro-1,1-difluoroacetone, 1.5 area % of 1,1,3,3-tetrachloro-1-fluoroacetone, 6.4 area % of 1,1,2-trichloro-2,2-difluoroethane, 0.3 area % of 1,1,2,2-tetrachloro-1-fluoroethane, and other substances.

EXAMPLE 4

A 2-liter autoclave made of stainless steel (SUS 316L) equipped with a reflux condenser and a stirrer was charged with 52 g of tin tetrachloride, 5.4 g of niobium pentachloride and 440 g of hydrogen fluoride. Then, heating of the autoclave was started upon which the temperature of a content (liquid) of the autoclave was reached to 40° C. Stirring of the content of the autoclave was continued for 1 hour from a time at which the temperature of the content had reached 40° C. Then, the autoclave was further charged with 485 g of pentachloroacetone as raw material. Then, the autoclave was again heated to gradually raise the inside temperature of the autoclave thereby allowing reaction of the content in the autoclave to be initiated. Upon lapse of 9 hours after initiation of the reaction, the inside temperature and pressure of the autoclave reached respectively 140° C. and 35 kg/cm$^2$ (gage pressure), in which the reaction was continued maintaining the pressure at 35 kg/cm$^2$ (gage pressure) while hydrogen chloride was emitted through the reflux condenser. Upon lapse of 23 hours after initiation of the reaction, the moles of hydrogen chloride purged reached 3 times of the moles of the raw material. At this time, heating of the autoclave was stopped to cool the content of the autoclave. After cooling, the temperature of the reflux condenser was adjusted at 20° C., upon which the inside temperature of the autoclave was raised again to 50° C. so that hydrogen fluoride was distilled out. Thereafter, the inside temperature of the reactor was raised to 120° C. thereby conducting flash distillation without allowing the effluent to pass through the reflux condenser, thus obtaining 307 g of organic compounds. The thus obtained organic compounds were subjected to analysis using a gas chromatograph. As a result, it was confirmed that the organic compounds contained 68.5 area % of 3,3-dichloro-1,1,1-trifluoroacetone, 5.6 area % of 1-chloro-1,3,3,3-tetrafluoroacetone, 1.2 area % of 1,3,3-trichloro-1,1-difluoroacetone, 0.5 area % of 1,1,3,3-tetrachloro-1-fluoroacetone, 2.6 area % of 1,1,2-trichloro-2,2-difluoroethane, 5.0 area % of 1,1,2,2-tetrachloro-1-fluoroethane, and other substances.

What is claimed is:

1. A process of producing chlorofluoroacetones represented by a general formula

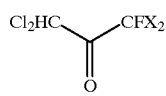

(1)

where X represents independently chlorine atom or fluorine atom, said process comprising:

fluorinating in a liquid phase pentachloroacetone by hydrogen fluoride in the presence of a catalyst comprising tin tetrahalide.

2. A process as claimed in claim 1, further comprising at least one compound comprising a metal selected from the group consisting of titanium, molybdenum, tantalum, lead, manganese, niobium, bismuth, tungsten, and iron.

3. A process as claimed in claim 1, wherein said catalyst includes tin tetrachloride and a compound selected from the group consisting of titanium tetrahalide and niobium pentachloride.

4. A process as claimed in claim 1, wherein said chlorofluoroacetone represented by the general formula (1) is a compound selected from the group consisting of 3,3-dichloro-1,1,1-trifluoroacetone and 1,1,3,3-tetrachloro-1-fluoroacetone.

5. A process as claimed in claim 1, wherein said chlorofluoroacetone represented by the general formula (1) is 3,3-dichloro-1,1,1-trifluoroacetone.

6. A process as claimed in claim 4, wherein said fluorinating is carried out at a temperature within a range of from about 50° C. to about 250° C.

7. A process as claimed in claim 4, wherein said fluorinating is carried out at a temperature within a range of from about 100° C. to about 200° C.

8. A process as claimed in claim 4, wherein said fluorinating is carried out at a temperature within a range of from about 130° C. to about 170° C.

9. A process as claimed in claim 6, wherein said fluorinating is carried out at a pressure within a range of from 1 kg/cm$^2$ to 100 kg/cm$^2$.

10. A process as claimed in claim 6, wherein the molar ratio of hydrogen fluoride to said chlorofluoroacetone represented by the general formula (1) is within a range of from 3 to 50.

11. A process as claimed in claim 6, wherein the molar ratio of hydrogen fluoride to said chlorofluoroacetone represented by the general formula (1) is within a range of from 8 to 20.

12. A process of producing chlorofluoroacetones represented by a general formula

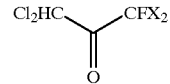

where X represents independently chlorine atom or fluorine atom, said process comprising:

fluorinating in a liquid phase pentachloroacetone by hydrogen fluoride in the presence of a catalyst comprising tin tetrahalide and at least one compound containing a metal selected from the group consisting of titanium, molybdenum, tantalum, lead, manganese, niobium, bismuth, tungsten, and iron.

* * * * *